(12) United States Patent
Vazquez Romaguera et al.

(10) Patent No.: US 12,427,340 B2
(45) Date of Patent: Sep. 30, 2025

(54) METHODS AND SYSTEMS FOR RECONSTRUCTING A 3D ANATOMICAL STRUCTURE UNDERGOING NON-RIGID MOTION

(71) Applicant: ECOLE POLYTECHNIQUE DE MONTREAL, Montreal (CA)

(72) Inventors: Liset Vazquez Romaguera, Montréal (CA); Tal Mezheritsky, Saint-Eustache (CA); Samuel Kadoury, Mount Royal (CA)

(73) Assignee: ECOLE POLYTECHNIQUE DE MONTREAL, Montreal (CA)

( * ) Notice: Subject to any disclaimer, the term of this patent is extended or adjusted under 35 U.S.C. 154(b) by 306 days.

(21) Appl. No.: 17/911,294

(22) PCT Filed: Mar. 17, 2021

(86) PCT No.: PCT/CA2021/050355
§ 371 (c)(1),
(2) Date: Sep. 13, 2022

(87) PCT Pub. No.: WO2021/184118
PCT Pub. Date: Sep. 23, 2021

(65) Prior Publication Data
US 2023/0129194 A1    Apr. 27, 2023

Related U.S. Application Data

(60) Provisional application No. 62/990,739, filed on Mar. 17, 2020.

(51) Int. Cl.
*A61N 5/10*    (2006.01)

(52) U.S. Cl.
CPC ......... *A61N 5/1049* (2013.01); *A61N 5/1067* (2013.01); *A61N 5/103* (2013.01)

(58) Field of Classification Search
None
See application file for complete search history.

(56) References Cited

U.S. PATENT DOCUMENTS

2004/0070582 A1  4/2004  Smith et al.
2006/0235287 A1  10/2006 Desmedt et al.
(Continued)

OTHER PUBLICATIONS

Santhanam, Anand, Modeling, simulation, and visualization of three-dimensional lung dynamics, 2006, Electronic Theses and Dissertations, University of Central Florida.
(Continued)

*Primary Examiner* — Edwin C Gunberg
(74) *Attorney, Agent, or Firm* — NORTON ROSE FULBRIGHT CANADA LLP

(57) ABSTRACT

There are described methods and systems for reconstructing a 3D anatomical structure undergoing non-rigid motion. The method comprises obtaining a 3D reference volume of the anatomical structure of the body, the reference volume corresponding to the anatomical structure at a reference phase of a respiratory cycle; acquiring 2D images of the anatomical structure at m prior times $T_{in} = \{t-m, \ldots, t-2, t-1\}$; estimating a set of deformations of the 3D reference volume at times n future $T_{out} = \{t, t+1, \ldots, t+n\}$ from a previously learned probability distribution conditioned on partial observations and anatomical information; applying a spatial transformation to the 3D reference volume based on the set of deformations; and displaying the reference volume post-spatial transformation as a motion-compensated anatomical structure for each time step $i \in T_{out}$.

20 Claims, 8 Drawing Sheets

(56) References Cited

U.S. PATENT DOCUMENTS

| | | |
|---|---|---|
| 2010/0191541 A1 | 7/2010 | Prokoski |
| 2011/0152684 A1 | 6/2011 | Altmann et al. |
| 2012/0148135 A1 | 6/2012 | Van Rens et al. |

OTHER PUBLICATIONS

Rueckert, Frangi, Schnabel, Automatic construction of 3-D statistical deformation models of the brain using nonrigid registration, IEEE Transactions Medical Imaging, 22-8, 1014-1025, 2003.

Balakrishnan, Zhao, Sabuncu, Guttag, Dalca, VoxelMorph: A Learning Framework for Deformable Medical Image Registration, IEEE Transactions Medical Imaging, 38-8, 1788-1800, 2019.

Hu, Hoffman, Reindhart, Automatic lung segmentation for accurate quantitation of volumetric X-ray CT images. IEEE Trans Med Imaging., 20-6, 490-498, 2001.

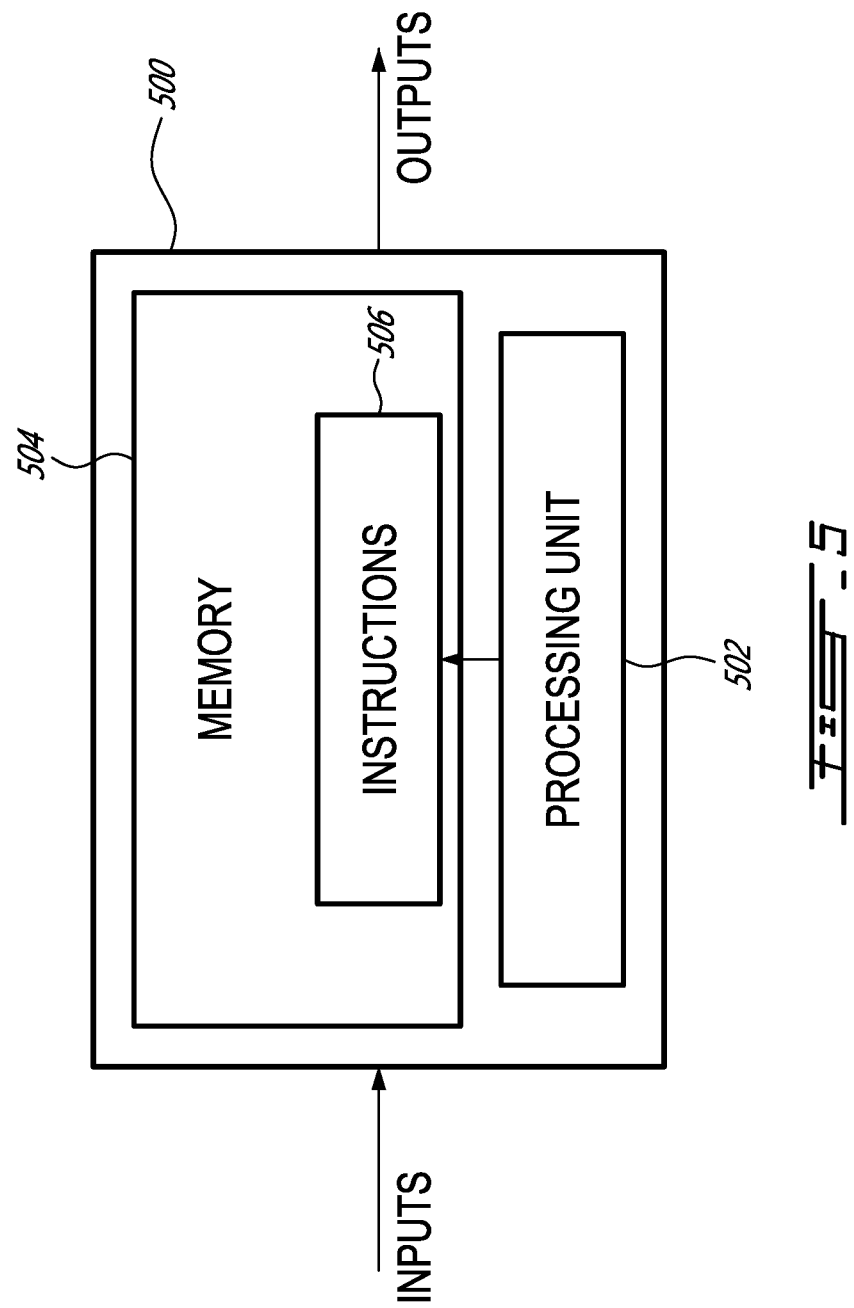

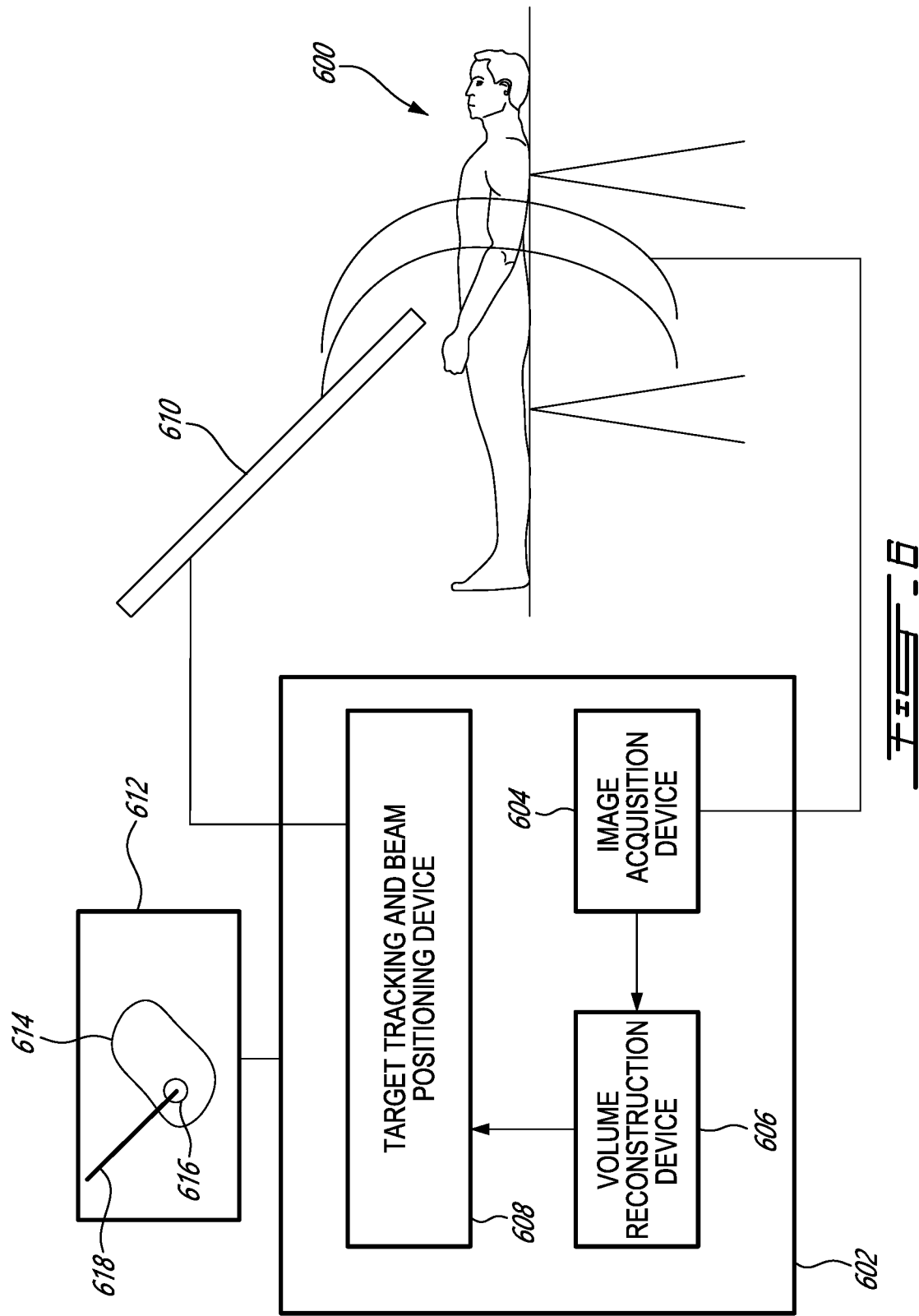

METHODS AND SYSTEMS FOR RECONSTRUCTING A 3D ANATOMICAL STRUCTURE UNDERGOING NON-RIGID MOTION

CROSS-REFERENCE TO RELATED APPLICATIONS

The present application is a US National Stage of International Application No. PCT/CA2021/050355, filed on Mar. 17, 2021, which claims the benefit of U.S. Provisional Patent Application No. 62/990,739 filed on Mar. 17, 2020, the contents of which are hereby incorporated by reference in their entirety.

TECHNICAL FIELD

The present disclosure relates generally to motion prediction and anatomy reconstruction to account for non-rigid motion.

BACKGROUND OF THE ART

Primary liver tumor, known as hepatocellular carcinoma, and secondary liver tumor (metastasis) represent, in aggregate, the second most common cause of cancer-related mortality in North America and the leading cause of cancer deaths worldwide, accounting for more than 600,000 deaths each year. Liver cancer is on the rise in Canada, with 24,400 new cases and 9,300 associated deaths in 2014. In parallel, the rate of liver metastases (LM) has also increased. LMs develop in 45% of patients with colorectal carcinoma (CRC) and currently represent a major health challenge, with 22,500 new cases in 2010 and 9,300 associated deaths. The economic burden for liver cancer (primary and secondary) is substantial and evaluated at 1.5 billion dollars/year in the USA/North America.

Enabling free-breathing liver cancer therapies such as external beam radiotherapy (EBRT) requires accurate tracking of the internal anatomy and tumor location during treatment in order to focus radiation beams on targets and avoid surrounding anatomy. Current technology for image-guided radiotherapy (e.g. MR-Linacs) is limited to only selecting 2D slices, which does not capture out-of-plane motion. Improvements in this field are needed.

SUMMARY

In accordance with a broad aspect, there is provided a method for reconstructing a 3D anatomical structure undergoing non-rigid motion. The method comprises obtaining a 3D reference volume of the anatomical structure of the body, the reference volume corresponding to the anatomical structure at a reference phase of a respiratory cycle; acquiring 2D images of the anatomical structure at m prior times $T_{in}=\{t-m, \ldots, t-2, t-1\}$; estimating a set of deformations of the 3D reference volume at times n future $T_{out}=\{t, t+1, \ldots, t+n\}$ from a previously learned probability distribution conditioned on partial observations and anatomical information; applying a spatial transformation to the 3D reference volume based on the set of deformations; and displaying the reference volume post-spatial transformation as a motion-compensated anatomical structure for each time step $i \epsilon T_{out}$.

In accordance with another broad aspect, there is provided a system for reconstructing a 3D anatomical structure undergoing non-rigid motion. The system comprises at least one processor and a non-transitory computer-readable medium having stored thereon program instructions. The program instructions are executable by the at least one processor for obtaining a 3D reference volume of the anatomical structure of the body, the reference volume corresponding to the anatomical structure at a reference phase of a respiratory cycle; acquiring 2D images of the anatomical structure at m prior times $T_{in}=\{t-m, \ldots, t-2, t-1\}$; estimating a set of deformations of the 3D reference volume at times n future $T_{out}=\{t, t+1, \ldots, t+n\}$ from a previously learned probability distribution conditioned on partial observations and anatomical information; applying a spatial transformation to the 3D reference volume based on the set of deformations; and displaying the reference volume post-spatial transformation as a motion-compensated anatomical structure for each time step $i \epsilon T_{out}$.

In accordance with yet another broad aspect, there is provided image-guided radiotherapy system comprising an image acquisition device for acquiring 2D images of the anatomical structure at times $T_{in}=\{t-m, \ldots, t-2, t-1\}$; a volume reconstruction device in accordance with the system for reconstructing a 3D anatomical structure undergoing non-rigid motion; and a target tracking and beam positioning device for tracking a tumor target in the anatomical structure and positioning a radiation beam at an expected position of the tumor target for each time step $i \epsilon T_{out}$.

Features of the systems, devices, and methods described herein may be used in various combinations, in accordance with the embodiments described herein.

BRIEF DESCRIPTION OF THE DRAWINGS

Reference is now made to the accompanying figures in which:

FIG. 5 is a block diagram of an example computing device; and

FIG. 6 is a schematic illustrating an example of the system for reconstructing a 3D anatomical structure undergoing non-rigid motion integrated with an image-guided radiotherapy system.

It will be noted that throughout the appended drawings, like features are identified by like reference numerals.

DETAILED DESCRIPTION

Figure 1A:
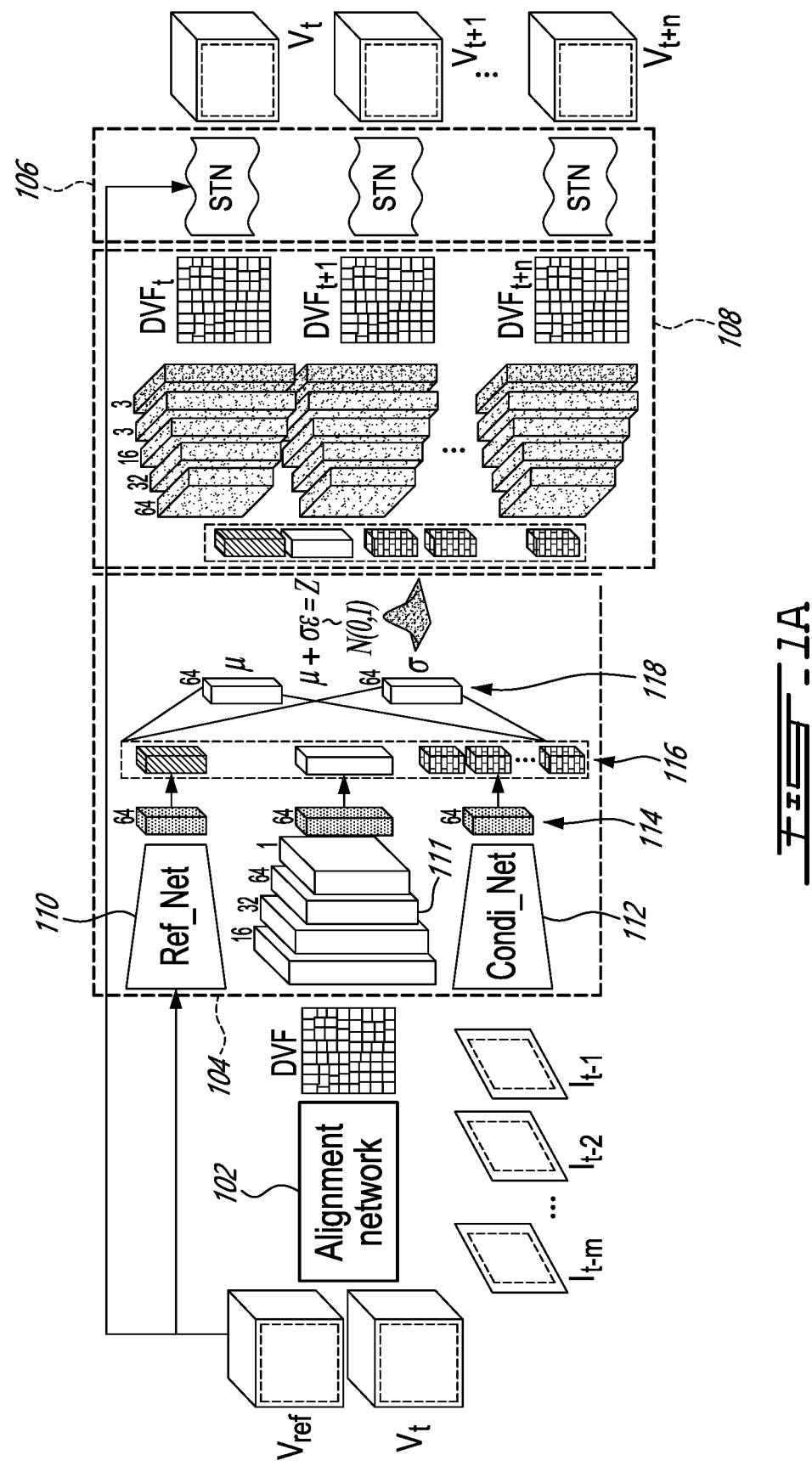
FIGS. 1A-1B illustrate examples of deep generative models for volumetric predictions from partial observations during training phases.

When performing various medical procedures, such as external beam radiotherapy (EBRT), a radiation oncologist will use multi-planar (in axial and coronal planes) 2D images of the targeted organ and its internal and surrounding structures (blood vessels, kidney, etc) acquired prior to the intervention. Images obtained during the procedure may also be used. However, a major limitation of vascular and focal interventions resides in the patient's respiration or involuntary movement, which may stray the pre-defined target and trajectories determined during planning from the actual anatomy, thus inducing errors in the relative position of the instrument performing the action with respect to the target.

Furthermore, live motion tracking of the internal anatomy depends on 3D imaging and image post-processing in real-time, which is challenging during interventional procedures. Some intraoperative acquisitions require a contrast agent, which is problematic as it may increase the toxicity of the patient. Clinicians therefore avoid using such intraoperative images as much as possible. Instead, they visually measure how the tumor target moves with intraoperative images at the beginning of the intervention, and then use their intuition of the internal motion of a tumor with regards to the therapeutic tool in order to achieve a proper targeting.

Some methods in image registration attempt to co-align pre-operative images with intra-operative acquisitions, but are limited to providing a static intraoperative representation of organ deformation due to real-time constraints to perform an image registration during the intervention. It is therefore difficult for a physician to use these techniques to obtain the location of anatomical structures in real-time and help predict the new location of the tumor.

There is described herein methods and systems for reconstructing a 3D anatomical structure of a body. The 3D reconstruction is intended to compensate for non-rigid motion of the anatomical structure, such as motion induced by breathing and/or swallowing. The anatomical structure may be in the abdomen, such as a liver, a kidney, a uterus, a prostate, or a lung. The anatomical structure may be in the neck or the head. The anatomical structure may be an organ, a muscle (for example in a limb (arm or leg) or elsewhere in the body), or a combination of various anatomical features.

The reconstruction techniques may be applicable to any anatomical structure that undergoes non-rigid motion, which is to be understood as motion that does not preserve the shape of the anatomical structure. The body may be human or animal. The reconstruction technique described herein addresses the problem of volume reconstruction, for example during radiotherapy treatments. A model is trained end-to-end to learn a distribution of realistic motion fields over a population data which allows for better uncertainty estimation during a volume generation phase. Furthermore, the distribution is conditioned on partial observations to recover the deformation at a given respiratory phase.

The method does not require supervised information such as ground truth registration fields, segmentation or anatomical landmarks. The reconstruction technique enables the tracking of targets that displace in 3D from 2D images acquired in real-time. The 2D images may be acquired using a wide variety of imaging technologies, such as but not limited to magnetic resonance imaging (MRI), computed tomography (CT), ultrasound, and the like. Providing volumetric information during radiotherapy treatments can improve the tracking of the target which ultimately increases the treatment efficiency and reduces damage to healthy tissues.

The system receives as input a 3D reference volume of the anatomical structure of the body, the reference volume corresponding to the anatomical structure at a reference phase of a respiratory cycle. The system also receives as input 2D images of the anatomical structure acquired at m prior times $T_m=\{t-m, \ldots, t-2, t-1\}$ to estimate a set of deformations of the 3D reference volume at n future times $T_{out}=\{t, t+1, \ldots, t+n\}$ by sampling a previously learned probability distribution conditioned on partial observations and anatomical information. The 2D images act as predictive variables to recover a dense displacement vector field (DVF) corresponding to a future respiratory phase. A spatial transformation is applied to the 3D reference volume based on the set of predicted deformations, and the reference volume post-spatial transformation is displayed as the motion-compensated anatomical structure for each time step $i \in T_{out}$.

FIG. 1A illustrates schematically a first embodiment for the training phase of the 3D reconstruction system. In this embodiment, a reference volume $V_{ref}$ taken at a reference respiratory phase is input into an alignment network 102. A training volume $V_t$ corresponding to any other respiratory phase is also input into the alignment network 102. Each volume $V_{ref}$, $V_t$ is composed of several stacked 2D images of a given imaging technology, such as MRI, CT, ultrasound, etc. During the training phase, $V_t$ may be constructed using a training dataset. For the alignment network 102, since the method does not rely on any surface-based information (i.e. prior segmentation) and to avoid explicit voxel generation, deformation between pairs of volumes over a population dataset are used. A registration function parameterized with a neural network is used to find the motion-induced deformation of the anatomical structure between the reference phase and the rest of the volumes within a time-resolved volumetric dataset. In the initial experiments, a Unet-like architecture with pre-trained weights was used. However, any other similar configuration can be used, i.e. any differentiable module allowing for end-to-end training.

The estimated 3D deformation between $V_{ref}$ and $V_t$ is fed to a motion encoder 104, which computes a feature representation through three sub-model networks 110, 111, 112. Subsequently, a set of deformations of the 3D reference volume at times $T_{out}=\{t, t+1, \ldots, t+n\}$ are estimated from partial observations and anatomical features as a conditional manifold learning task using a motion decoder 108. The predictive variables, i.e. the reference volume $V_{ref}$ and the images of the training volume $V_t$ ($I_{t-m}, \ldots I_{t-2}, I_{t-1}$) are integrated during optimization in the form of conditional variables which modulate the motion distribution learned by the model. Let $M=\{\Phi_t, \Phi_{t+1}, \ldots, \Phi_{t+n}\}$ be a set of displacement vector fields yielded by the alignment network, $V_{ref}$ the reference volume and $I_s=[I_{t-1}, I_{t-2}, \ldots, I_{t-m}]$ the surrogate image sequence. The goal of the model is to learn the conditional distribution $P(M|I_s, V_{ref})$ to produce a set of displacements M given the available partial information and subject anatomy. Following the generative process of conditional variational autoencoders, a latent variable z is generated from the prior distribution $p_\theta(z)$ which is constrained to be a Gaussian, i.e. $z \sim \mathcal{N}(o,I)$. Therefore, by randomly sampling values of z, new displacement vector fields can be generated. However, computing the posterior distribution $p_\theta(z|I_s, V_{ref})$ to obtain z is analytically intractable. Therefore, the motion encoder 104 is configured to find an approximation of the posterior:

$$q_\psi(z|I_s, V_{ref}) = \mathcal{N}(\mu(M,I_s,V_{ref}), \sigma(M,I_s,V_{ref})) \quad (1)$$

The motion encoder 104, parameterized with stacked 3D convolution layers, learns the mean $\mu \in \mathfrak{R}^d$ and diagonal covariance $\sigma \mu \in \mathfrak{R}^d$ from the data, as depicted in FIG. 1A. At training time, the sampling of z is made differentiable with respect to $\mu$ and $\sigma$ by using reparameterization, and by defining $z=\mu+\varepsilon \times \sigma$, where $\varepsilon \sim \mathcal{N}(o,I)$.

The distance between both distributions $p_\theta$ and $q_\psi$ can be minimized using the Kullback-Leibler (KL) divergence within a combined loss function which also seeks to minimize a reconstruction loss. Hence, the reference volume $V_{ref}$ is warped with the transformation provided by a decoder 108 enabling the model to calculate a similarity measure $\mathcal{L}_{sim}$ between $V_{ref} \cdot \Phi_t$ and the expected volume $V_t$. Stochastic gradient descent is used to find optimal parameters $\hat{\theta}$ by minimizing the following loss function:

$$\hat{\theta} = \operatorname{argmin}\left[\frac{1}{n}\sum_{i=t}^{i=t+n} \mathcal{L}_{sim}(V_{ref} \circ \Phi_i, V_i) + KL(q_\psi(z \mid I_s, V_{ref}) \| p_\theta(z))\right] \quad (2)$$

where the KL-divergence can be computed in closed form.

Figure 2:
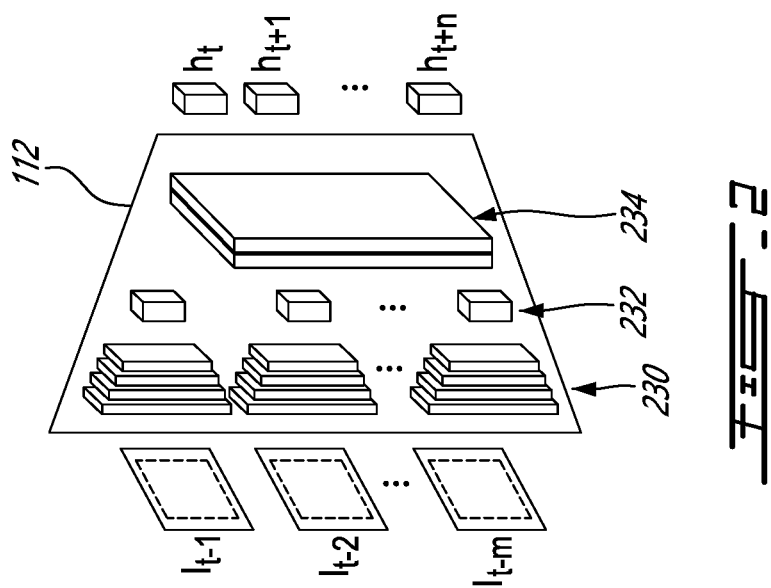
FIG. 2 illustrates an example architecture for a conditional network of the models of FIG. 1A-1B.
Figure 4:
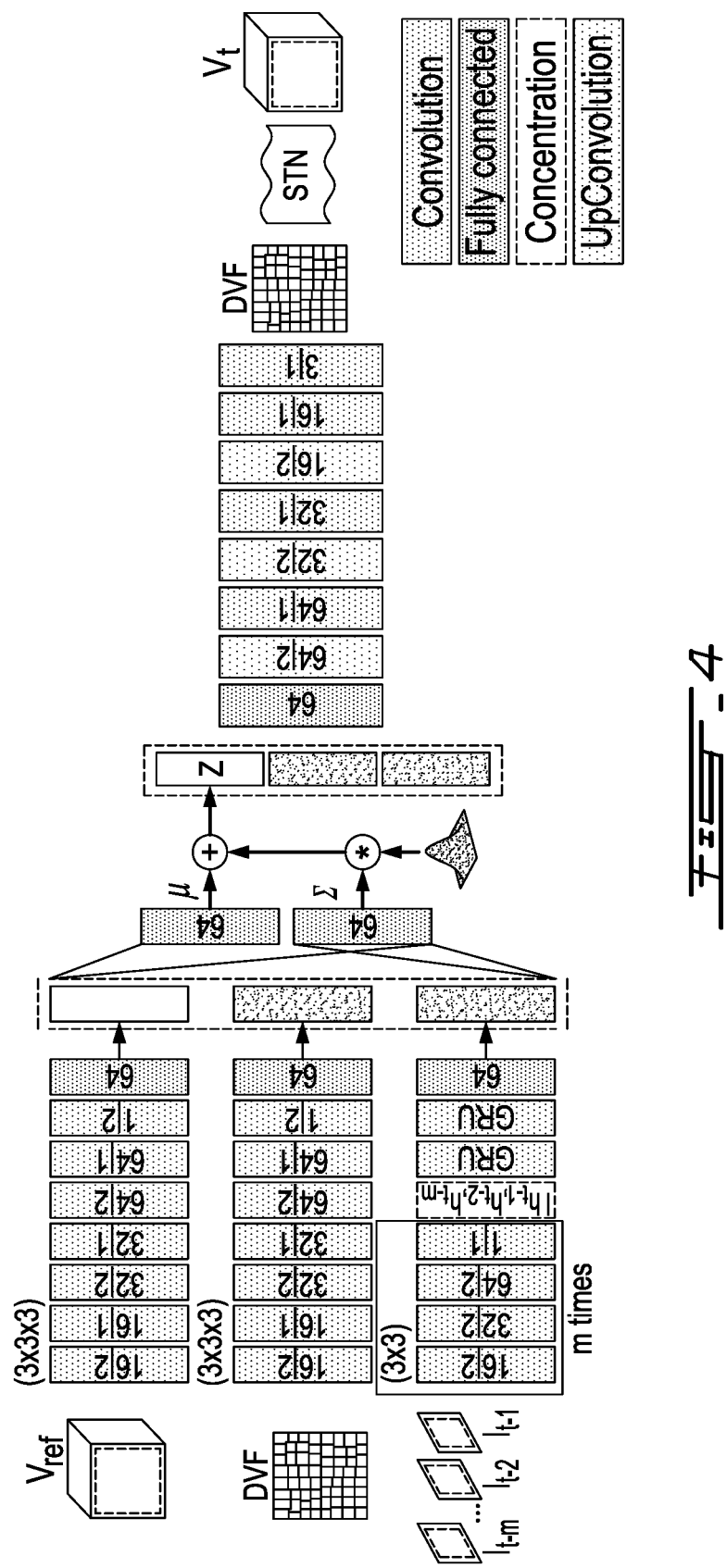
FIG. 4 is an example implementation in software of the deep generative model for volumetric predictions.

The structure of the sub-model networks 110, 111, 112 and motion decoder 108 resembles a conditional variational auto-encoder. In the illustrated architecture, a multi-branch convolutional neural network is used, composed of the three sub-models 110, 111, 112 that encode: (1) the motion fields provided by the alignment network 102 (sub-model 111), (2) a pre-treatment volume ("Ref-Net" or reference sub-network 110) and (3) the image surrogates ("Condi-Net" or conditional sub-network 112). The first and second sub-model networks 110, 111 have an identical configuration, an example of which is illustrated in FIG. 4. The third sub-model ("Condi-Net"), shown in FIG. 2, is composed of m stacks 230 of 2D convolutions with kernel size 3×3×3 and stride of 2 followed by ReLU activations and batch normalization (BN). Condi-Net 112 acts as a temporal predictor. Each one of the stacks 230 independently processes the channel-wise concatenation of a single temporal image with its corresponding slice in the reference volume. The temporal representations are concatenated together at 232 and fed to a convolutional gated recurrent unit 234 which leverages the spatiotemporal information to extrapolate a feature vector on time. Alternatives predictors, such as Convolutional Long Short-Term Memory (ConvLSTM) or attention-based mechanism (e.g. Transformers) can also be used. Referring back to FIG. 1A, each one of the aforementioned branches end in a fully connected (FC) layer 114. Their respective outputs are further concatenated at 116 and mapped to two additional FC layers at 118 to generate $\mu$ and $\sigma$ which are combined with $\varepsilon$ to construct the latent space sample z.

The decoder 108, also modeled with a convolutional neural network, reconstructs the displacement vector field given the reference volume and the temporal slices. The conditional dependency is explicitly modeled by the concatenation of z with the feature representation of $V_{ref}$ and $I_s$. At test time, the decoder 108 operates as a generative reconstruction network given the patient anatomy and the cine-2D acquisition yielding realistic DVFs by sampling z~ $\mathcal{N}$(o,I).

Finally, the estimated DVFs are used to resample the reference volume into a set of warped volumes that match the target volumes $V_t, V_{t+1}, \ldots, V_{t+n}$ for optimization purposes. For this step, a differentiable spatial transformation module 106 is used, such as the one described in Balakrishnan, G., Zhao, A., Sabuncu, M. R., Guttag, J., Dalca, A. V.: Voxelmorph: a learning framework for deformable medical image registration. IEEE transactions on medical imaging 38(8), 1788-1800 (2019).

Figure 1B:
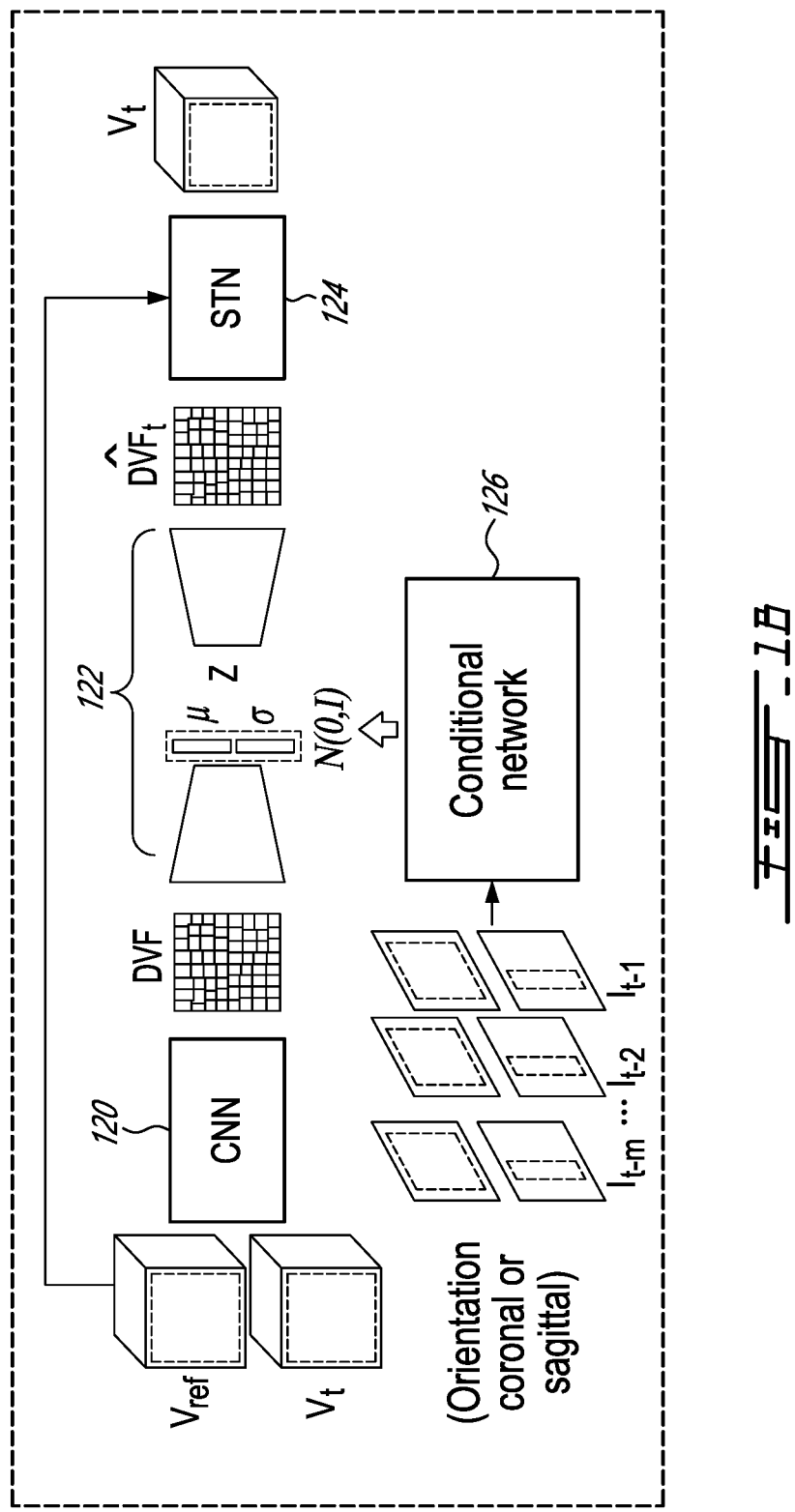

FIG. 1B illustrates an alternative embodiment for the architecture used for training the 3D reconstructing system. Convolution Neural Network(s) (CNN) 120 learn the deformation between both input volumes, $V_{ref}$ and $V_t$. The deformation is mapped to a latent space described by a probability distribution through a conditional variational auto-encoder 122. During training, the objective is to minimize the KL divergence between the learned distribution and the prior. The latent space is conditioned on a feature vector computed from surrogate images, i.e. sagittal or coronal slices $I_s=[I_{t-1}, I_{t-2}, \ldots, I_{t-m}]$ via a conditional network 126. The generated volume $V_t$ is obtained by warping the reference volume $V_{ref}$ with the predicted deformation $D\hat{V}F_t$ using a spatial transformation network 124. The embodiment of FIG. 1B is optimized by minimizing the following composite loss function:

$$\mathfrak{R}_{total} = \mathfrak{R}_{sim}(V_{ref}D\hat{V}F_t, V_t) + \nu KL(z, N(0,I)) \quad (3)$$

Where $V_{ref}$ is a reference 3D volume, $D\hat{V}F_t$ is the predicted displacement field at time t, $V_t$ is the ground-truth 3D volume, $\mathfrak{R}_{sim}$ is a similarity metric (e.g. Mean Squared Error, Normalized Cross Correlation), $\nu$ is a regularization weight and KL(z,N(0,I)) represents the Kullback-Leibler distance between the posterior distribution (z-vector) and the Gaussian prior N(0,I).

Figure 3A:
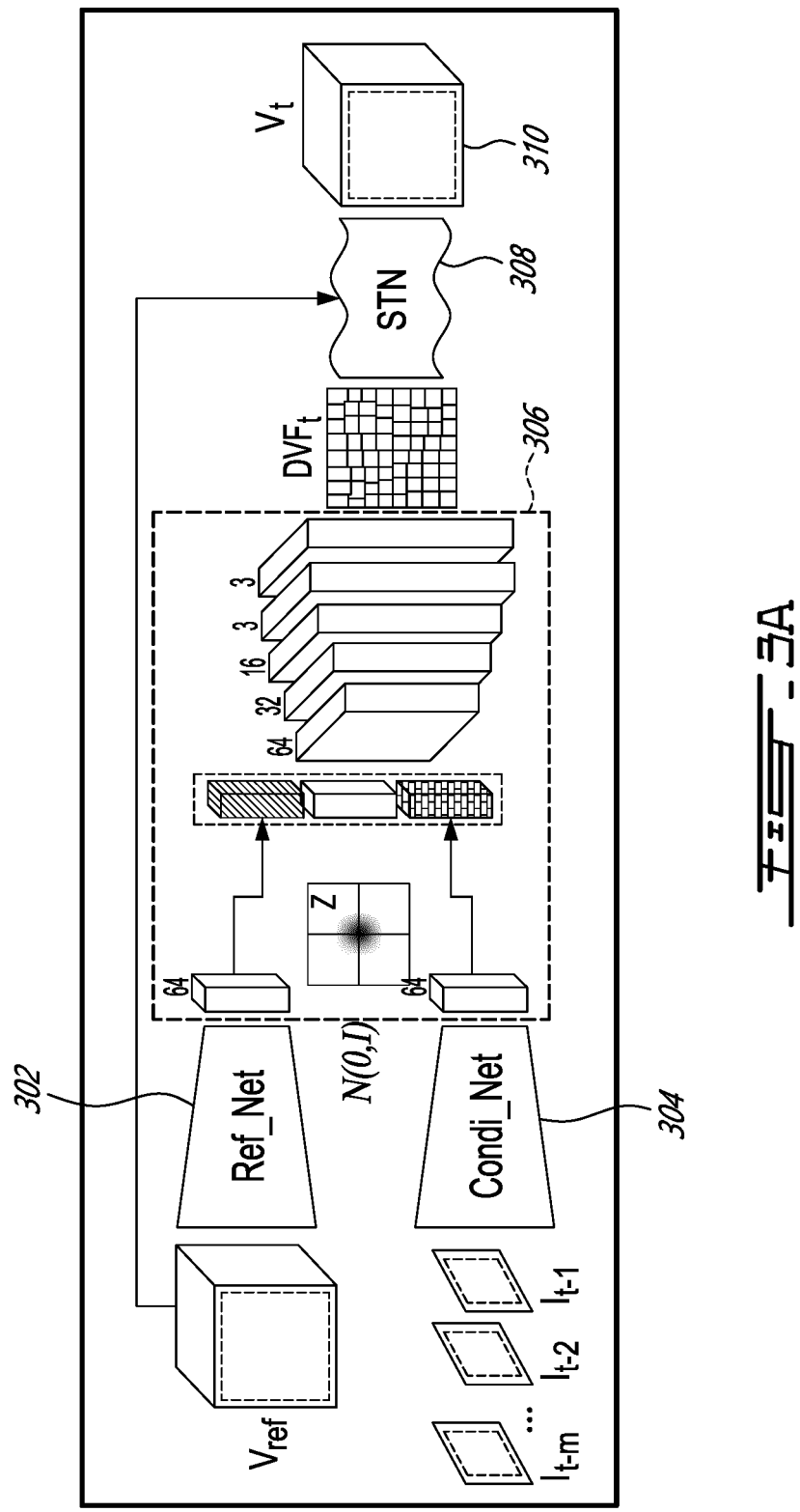
FIGS. 3A-3B illustrate examples of architectures for reconstructing 3D anatomical structures undergoing non-rigid motion using a probability distribution learned from the models of FIGS. 1A and 1B, respectively.

FIG. 3A illustrates the testing architecture that corresponds to the training architecture of FIG. 1A. The 3D reference volume $V_{ref}$ of the anatomical structure is received at a reference network 302, the 2D images of the anatomical structure obtained at times $T_{in}=\{t-m, \ldots, t-2, t-1\}$ are received at a conditional network 304. A set of deformations of the 3D reference volume are estimated by the decoder 306, at times $T_{out}=\{t, t+1, \ldots, t+n\}$ from the previously learned probability distribution conditioned on partial observations and anatomical information. A spatial transformation is applied to the 3D reference volume using the warping layer 308 based on the set of deformations. The reference volume post-spatial transformations 310 (i.e. the generated volumes $V_t, V_{t+1}, \ldots, V_{t+n}$) are then displayed as the anatomical structure at times $T_{out}=\{t, t+1, \ldots, t+n\}$.

Figure 3B:
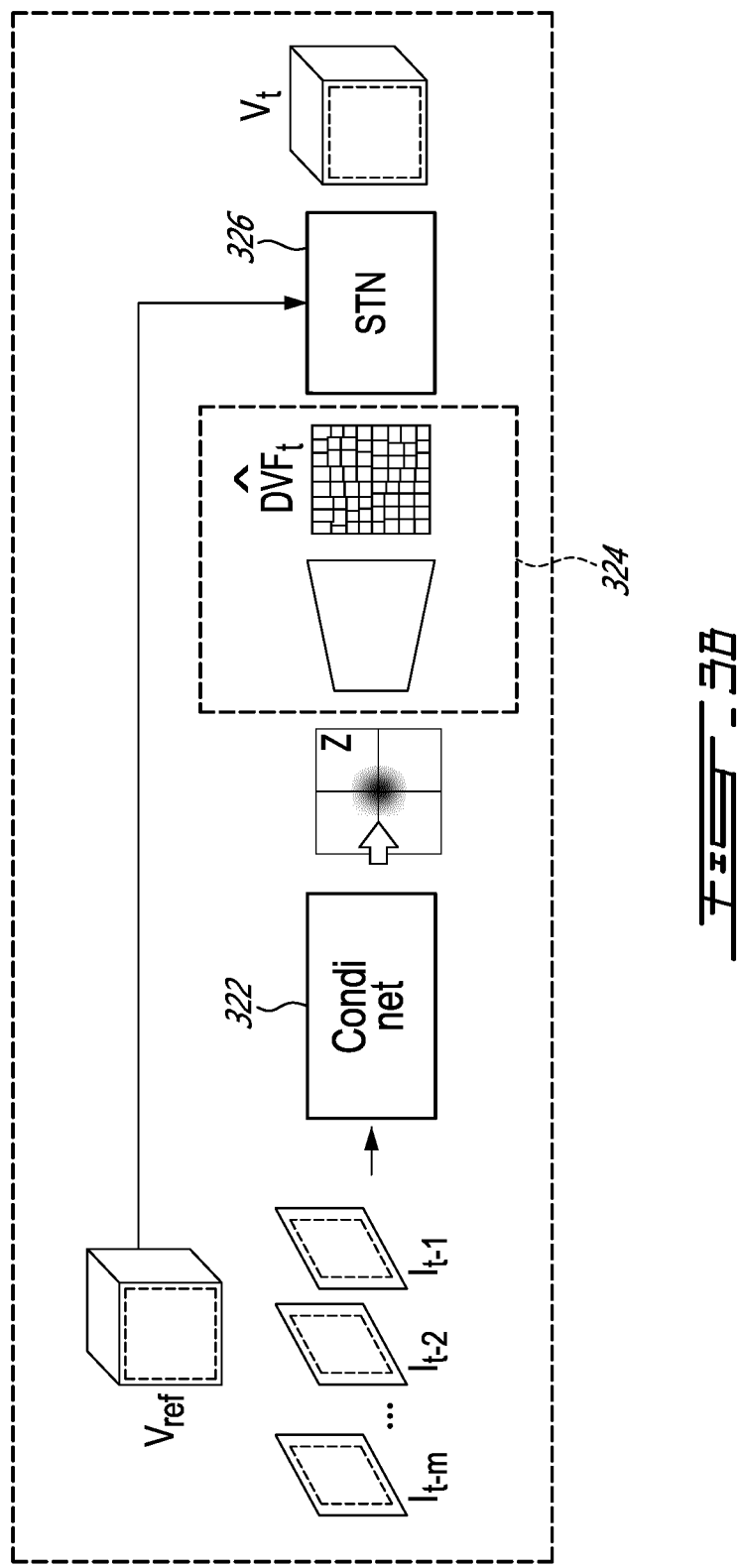

FIG. 3B illustrates the testing architecture that corresponds to the training architecture of FIG. 1C. The 2D images of the anatomical structure obtained at times $T_{in}=\{t-m, \ldots, t-2, t-1\}$ are received at a conditional network 322. The predicted deformation from the previously learned probability distribution conditioned on partial observations is recovered by the decoder 324 and applied to the reference volume using the warping layer 326.

FIG. 4 illustrates a specific and non-limiting example of an implementation of the architecture that learns the conditional distribution $P(M|I_s, V_{ref})$ to produce the displacement matrix M given the available partial information and subject anatomy. This example illustrates a potential configuration for the layers and corresponding hyper-parameters based on the described conditional variational auto-encoder. It will be understood that other configurations are also contemplated.

With reference to FIG. 5, an example of a computing device 500 is illustrated for implementing one or more of the components illustrated in FIGS. 1-4. For example, any one of the alignment network 102, the motion encoder 104, the spatial transformation network 106, the decoder 108, the reference network 110, and the conditional network 112 may be implemented by one or more computing device 500.

The computing device 500 comprises a processing unit 502 and a memory 504 which has stored therein computer-executable instructions 506. The processing unit 502 may comprise any suitable devices such that instructions 506, when executed by the computing device 500 or other programmable apparatus, may cause the functions/acts/steps as described herein to be executed. The processing unit 502 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 504 may comprise any suitable known or other machine-readable storage medium. The memory 504 may comprise non-transitory computer readable storage medium, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions 506 executable by processing unit 502.

The methods may be implemented in a high-level procedural or object-oriented programming or scripting language, or a combination thereof. Alternatively, the methods may be implemented in assembly or machine language. The language may be a compiled or interpreted language. Program code for implementing the methods may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods may also be considered to be implemented by way of a non-transitory computer-readable storage medium having a computer program stored thereon. The computer program may comprise computer-readable instructions which cause a computer, or more specifically the processing unit 502 of the computing device 500, to operate in a specific and pre-defined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically, the functionality of the program modules may be combined or distributed as desired in various embodiments.

In some embodiments, the methods and systems described herein allow the reconstruction of a 3D MRI volume from partial 2D Cine-MRI images using a conditional variational auto-encoder architecture along with a spatial transformation network layer. Providing up-to-date volumetric MRI information during radiotherapy treatment, such as free-breathing radiation therapy, can improve the tracking of the treatment target which ultimately improves the treatment efficiency and reduces damages to healthy tissues surrounding the target. Indeed, the methods and systems described herein allow to track targets that displace in 3D using only 2D cine-MRI images acquired in real-time. A distribution of realistic motion fields is learned, which allows for better uncertainty estimation during the volume generation phase. A complete 3D anatomical volume with grayscale voxel intensities (non-binarized) may be generated, and no prior segmentation or additional manual steps are required.

The methods and systems described herein provide a computational framework for reliable and rapid organ movement and deformation tracking. This may lead to increased accuracy and reduced radiation time. The notions described herein may be integrated in radiotherapy devices and may be useful to all types of interventions where analysis of respiratory movement and compensation is used, independently of the therapeutic modality or of the imaging modality used during the intervention. In some embodiments, the methods and system described herein are integrated with Magnetic Resonance Imaging Guided Linear Accelerator (MRI-Linac) applications, a hybrid technology that combines radiation and high-resolution MRI in a single machine. The real-time imaging capabilities of MRI (which serve as a navigator signal) may thus be exploited with the proposed model in order to improve the target localization during the breathing cycle observed in radiotherapy treatments.

The methods and systems described herein may form part of radiotherapy guidance systems and improve the efficacy of cancer treatments by increasing radiation concentration in tumor tissues and limiting systemic toxicity. This contributes to reducing side effects and morbidity, while avoiding multiple hospitalizations required to perform invasive whole-organ radiation treatments. The methods and systems may be integrated in a software tool that can predict the continuous displacement of tumor targets, thus compensating for breathing motion during dose delivery. For example, the methods and system may be integrated within a system which personalizes a patient's radiotherapy plan based on input imaging and navigation data. An example embodiment is illustrated in FIG. 6, where a patient 600 is undergoing image-guided radiation therapy. An image-guided radiation therapy system 602 comprises an image acquisition device 604 for obtaining 2D images of the patient 600 in real-time. These images are provided to a volume reconstruction device 606, which uses the principles described herein to reconstruct the 3D volume of the anatomical structure 614 of the patient 600 while compensating for tumor motion. The reconstructed 3D volume is provided to a target tracking and beam positioning device 608 which determines where to position the radiation beam 610 based on a predicted position of a tumor target 616 in the anatomical structure 614. The anatomical structure 614 and tumor target 616 may be displayed on a display device 612 with a beam image 618. The images are thus acquired at time T and the beam is positioned in accordance with where the tumor target will be at time T+Δt, where Δt is the delay between the image acquisition time and the application of the radiation beam.

The methods and systems can also be used for vascular procedures such as chemo-embolization which seeks to minimize the effect of vessel deformation during injection of anti-cancerous drugs, and would represent a way to address potential displacement of blood vessels during arterial therapies, which may be caused by respiratory motion or by peristalsis.

In some embodiments dedicated hardware with accelerated graphical processing units (GPU) are used for training models. In some embodiments, a dataset with a variety of breathing patterns and anatomies is used in order to have a good representation of the population that is treated. In some embodiments, the model is trained using a 4D MRI dataset. During training, a deep network learns the deformation that a certain organ undergoes from a pre-treatment volume to a time-resolved 4D dataset from a same subject. Displacement vector fields are mapped to a latent space creating a motion probability distribution over a population dataset, and the latent space is conditioned on surrogates in the form of cine-MRI scans to infer the global anatomy. A trained model warps a gated 3D pre-operative acquisition by sampling deformations conditioned on in-room 2D cine-MRI scans to reconstruct a 3D anatomy at future times, thereby compensating for system latencies and reducing geometric uncertainties during image-guided radiotherapy.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the systems and methods described herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be apparent to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for reconstructing of, and target tracking and beam positioning in, a 3D anatomical structure undergoing non-rigid motion, the method comprising:
    obtaining a 3D reference volume of the anatomical structure of the body, the reference volume corresponding to the anatomical structure at a reference phase of a respiratory cycle;
    acquiring 2D images of the anatomical structure at m prior times $T_{in}=\{t-m, \ldots, t-2, t-1\}$;
    estimating a set of deformations of the 3D reference volume at n future times $T_{out}=\{t, t+1, \ldots, t+n\}$ from a previously learned probability distribution conditioned on partial observations and anatomical information;
    applying a spatial transformation to the 3D reference volume based on the set of deformations;
    displaying the reference volume post-spatial transformation as a motion-compensated anatomical structure for each time step $i \epsilon T_{out}$;
    tracking, based on the reference volume post-spatial transformation, a target displacing in the anatomical structure; and
    positioning a treatment beam at an expected position of the target for each time step $i \epsilon T_{out}$.

2. The method of claim 1, wherein the reference phase of the respiratory cycle is an exhale phase.

3. The method of claim 1, wherein the probability distribution is learned from a conditional variational auto-encoder architecture.

4. The method of claim 1, wherein the 2D images are magnetic resonance images.

5. The method of claim 1, wherein the anatomical structure comprises a tumor target.

6. The method of claim 1, wherein the anatomical structure is a liver or a lung.

7. The method of claim 1, wherein the method is performed during radiotherapy treatments.

8. The method of claim 7, wherein the radiotherapy is external beam radiotherapy.

9. The method of claim 7, wherein the 2D images are acquired in real-time during the radiotherapy treatments.

10. A system for reconstructing of, and target tracking and beam positioning in, a 3D anatomical structure undergoing non-rigid motion, the system comprising:
    at least one processor; and
    a non-transitory computer-readable medium having stored thereon program instructions executable by the at lest one processor for:
    obtaining a 3D reference volume of the anatomical structure of the body, the reference volume corresponding to the anatomical structure at a reference phase of a respiratory cycle;
    acquiring 2D images of the anatomical structure at m prior times $T_{in}=\{t-m, \ldots, t-2, t-1\}$;
    estimating a set of deformations of the 3D reference volume at n future times $T_{out}=\{t, t+1, \ldots, t+n\}$ from a previously learned probability distribution conditioned on partial observations and anatomical information;
    applying a spatial transformation to the 3D reference volume based on the set of deformations; and
    displaying the reference volume post-spatial transformation as a motion-compensated anatomical structure for each time step $i \epsilon T_{out}$;
    tracking, based on the reference volume post-spatial transformation, a target displacing in the anatomical structure; and
    positioning a treatment beam at an expected position of the target for each time step $i \epsilon T_{out}$.

11. The system of claim 10, wherein the reference phase of the respiratory cycle is an exhale phase.

12. The system of claim 10, wherein the probability distribution is learned from a conditional variational auto-encoder architecture.

13. The system of claim 10, wherein the 2D images are magnetic resonance images.

14. The system of claim 10, wherein the anatomical structure comprises a tumor target.

15. The system of claim 10, wherein the anatomical structure is a liver or a lung.

16. The system of claim 10, wherein the 3D anatomical structure is reconstructed during radiotherapy treatments.

17. The system of claim 16, wherein the radiotherapy is external beam radiotherapy.

18. The system of claim 16, wherein the 2D images are acquired in real-time during the radiotherapy treatments.

19. An image-guided radiotherapy system comprising:
    an image acquisition device for acquiring 2D images of the anatomical structure at times m prior $T_{in}=\{t-m, \ldots, t-2, t-1\}$;
    a volume reconstruction device in accordance with claim 10; and
    a target tracking and beam positioning device for tracking a tumor target in the anatomical structure and positioning a radiation beam at an expected position of the tumor target for each time step $i \epsilon T_{out}$.

20. The image-guided radiotherapy system of claim 19, wherein the system is a Magnetic Resonance Imaging Guided Linear Accelerator.

* * * * *